United States Patent [19]

Wei et al.

[11] 4,302,585
[45] Nov. 24, 1981

[54] 3-HYDROXY-3-SUBSTITUTED PHENYLTHIAZOLO[2,3-B]QUINAZOLINE-2-ALKANOIC ACIDS AND THEIR LACTONES

[75] Inventors: Peter H. L. Wei, Springfield; Stanley C. Bell, Penn Valley, both of Pa.

[73] Assignee: American Home Products Corporation, New York, N.Y.

[21] Appl. No.: 218,904

[22] Filed: Dec. 22, 1980

[51] Int. Cl.$^3$ ............... C07D 513/04; C07D 513/14; A61K 31/505

[52] U.S. Cl. ............................................. 544/247

[58] Field of Search ..................... 544/247; 424/251

[56] References Cited

U.S. PATENT DOCUMENTS

| | | | |
|---|---|---|---|
| 3,853,872 | 12/1974 | Wei et al. | 424/251 X |
| 3,947,439 | 3/1976 | Wei et al. | 544/250 |
| 4,168,380 | 9/1979 | LeMahieu | 544/250 |
| 4,214,089 | 7/1980 | Fenichel et al. | 548/151 |

FOREIGN PATENT DOCUMENTS 849542  6/1977  Belgium .

OTHER PUBLICATIONS

Bell et al., J. Med. Chem., vol. 19 (4), pp. 524–530 (1976).

*Primary Examiner*—Donald G. Daus
*Assistant Examiner*—Diana G. Rivers
*Attorney, Agent, or Firm*—George Tarnowski

[57] ABSTRACT

3-Hydroxy-3-substituted phenylthiazolo[2,3-b]quinazoline-2-acetic acids, their lactones and related compounds, and their use as immunomodulating agents are disclosed.

3 Claims, No Drawings

3-HYDROXY-3-SUBSTITUTED PHENYLTHIAZOLO[2,3-b]QUINAZOLINE-2-ALKANOIC ACIDS AND THEIR LACTONES

BRIEF DESCRIPTION OF THE INVENTION

The invention relates to 3-hydroxy-3-substituted phenylthiazolo[2,3-b]quinazoline-2-acetic acids, their lactones and related compounds, and their use as immunomodulating agents.

The compounds of the present invention are immunomodulating agents which exert an immunosuppressive effect on the immune system. As such, the compounds are especially indicated in the treatment of various skin graft and organ transplant reactions, and immune system diseases and disorders such as systemic lupus erythematosus (SLE) and rheumatoid arthritis.

DETAILED DESCRIPTION OF THE INVENTION

The invention is directed to novel compounds, having the general formula:

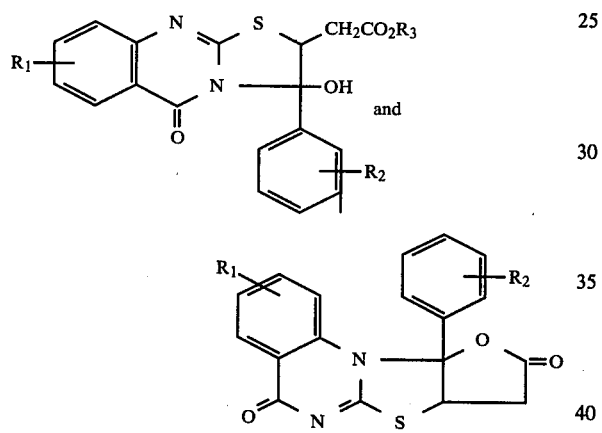

wherein $R_1$ is hydrogen, lower alkyl of 1-4 carbon atoms, $CF_3$, $NO_2$ and $NH_2$;

$R_2$ is hydrogen, lower alkyl of 1- carbon atoms $CF_3$, halo, cyclohexyl or phenyl;

$R_3$ is hydrogen or lower alkyl of 1-4 carbon atoms.

The term halo is meant to encompass fluoro, chloro, bromo and iodo.

The compounds of the invention having the general formula:

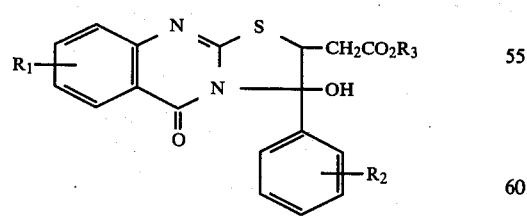

wherein $R_1$; $R_2$ and $R_3$ are as defined hereinbefore, are prepared by reacting an alkali metal salt of an appropriately substituted 2-mercapto-4(3H)-quinazolinone with an appropriately substituted 3-bromo-3-benzoyl-propionic acid or derivative thereof at room temperature according to the following sequence:

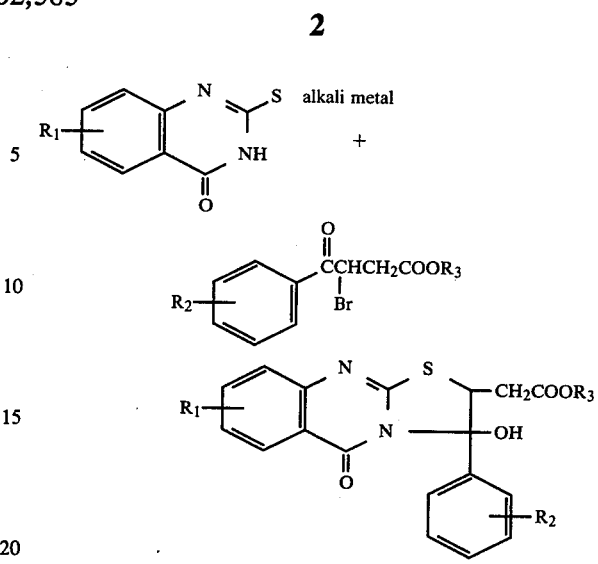

When the above reaction sequence is carried out in refluxing acetone, both the thiazolo[2,3-b]quinazoline acetic acid and its lactone are obtained:

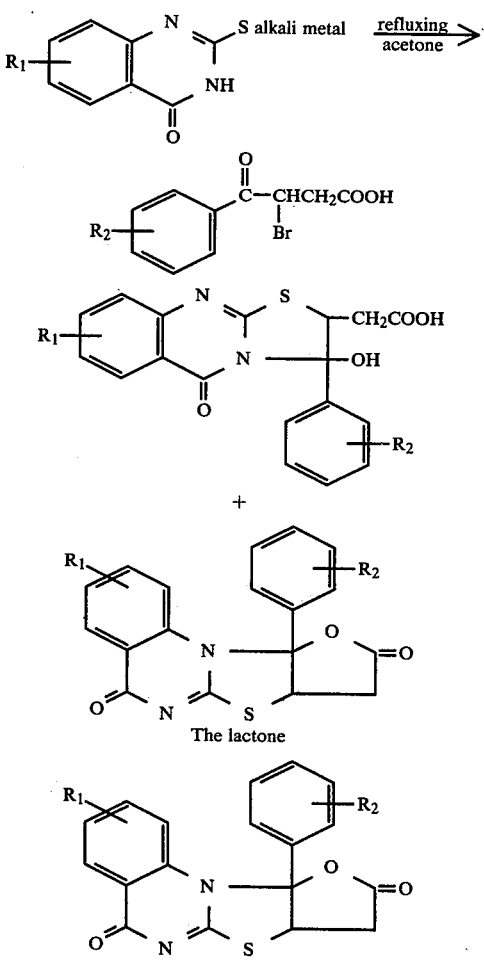

can be obtained directly from the thiazolo[2,3-b]quinazoline acetic acid prepared according to first described reaction sequence by treating the latter with an organic or inorganic acid, such as acetic, trifluoroacetic, hydrochloric, hydrobromide sulfuric and the like:

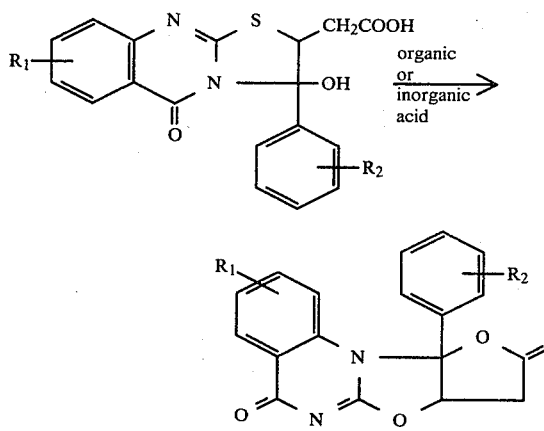

The starting compounds are either commercially available or can be readily prepared according to conventional chemical procedures.

The compounds of the invention are active immunomodulators, and so have therapeutic application in a variety of situations in which immunomodulation is indicated. Thus, the compounds are useful in treating allograft reactions, organ transplant reactions, and graft vs. host reactions. The compounds are also useful in the treatment of autoimmune disease, such as systemic lupus erythematosus (SLE). Further, the compounds of the invention inhibit the production of the immunoglobulins, which are so pathologic to autoimmune disease such as SLE, as well as the production of antigen-antibody complexes which are the causative agents of renal and inflammatory processes in arthritis and autoimmune diseases. Thus, the compounds of the invention are also useful in the treatment of such conditions as rheumatoid arthritis.

When the compounds of the invention are employed as immunomodulators, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth methyl cellulose, sodium carboxylmethyl cellulose, low melting wax, cocoa butter, and the like. Diluents, flavoring agents, solubilizers, lubricants, suspending agents, binders, tablet-disintegrating agents and the like may be employed. The compounds may be encapsulated with or without other carriers. In all cases the proportion of active ingredients in said compositions both solid and liquid will be at least sufficient to impart immunomodulatory activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration level that will generally afford effective results without causing any harmful or deleterious side effect.

The following examples show the preparation and pharmacological testing of compounds embraced by the invention.

EXAMPLE 1

3-(4-Chlorphenyl)-2,3-dihydro-3-hydroxy-5-oxo-5$\underline{H}$-thiazolo[2,3-b]quinazoline-2-acetic acid 12.9 g (0.06 m) of the potassium salt of 2-mercapto-4(3$\underline{H}$)-quinazoline and 19.0 g (0.06 m) of 3-bromo-3-(4-chlorobenzoyl) propionic acid are suspended in 1500 ml of acetone and the mixture is stirred at room temperature overnight. The solid is filtered off and the filtrate is concentrated to a small volume in vacuo. The solid (3.4 g) is collected and is found to be unreacted mercaptan. The filtrate is further concentrated to dryness and the residual solid obtained is triturated with 500 ml. anhydrous ether. The ether solution is filtered and the filtrate allowed to stand, after which the precipitated solid is collected to yield 4.6 g of title product, m.p. 180°–185° C.

Analysis for: $C_{18}H_{13}ClN_2O_4S$
Calculated: C, 55.60; H, 3.77; N, 7.21; Cl, 9.12;
Found: C, 55.90; H, 3.40; N, 7.19; Cl, 9.09.

EXAMPLE 2

10a-(4-chlorophenyl)-7a, 10a-dihydro-5$\underline{H}$-furo- [2', 3':4,5]thiazolo[3,2-a]-quinazoline-5,9-(8H)-dione 14.0 g (0.065 m) of the potassium salt of 2-mercapto-4(3$\underline{H}$)-quinazoline and 19.0 g (0.065 m) of 3-bromo-3-(4-chlorobenzoyl) propionic acid are suspended in 1500 ml of acetone and the mixture is heated for 8 hours. The solid is filtered off and the filtrate concentrated to dryness. The residual solid is triturated with 400 ml of anhydrous ether and 1.5 g of the title product is isolated, m.p. 215°–220° C.

Analysis for: $C_{18}H_{11}ClN_2O_3S$
Calculated: C, 58.30; H, 2.99; Cl, 9.56; N, 7.56; S, 9.03
Found: C, 58.52; H, 3.14; Cl, 9.22; N, 7.34; S, 9.03

From the ether washings of the last step above, 2.3 g of 3-(4-chlorophenyl)-2,3-dihydro-3-hydroxy-5-oxo-5$\underline{H}$-thiazolo[2,3b]quinazoline-2-acetic acid are also obtained.

EXAMPLE 3

The activity of the compounds is determined according to the following procedure:

T lymphocytes are isolated from spleens of 4 month old male CBA/J mice. Cell homogenates are prepared in Hank's balanced salt solution (HBSS). After removal of larger particles and repeated washing of the cells in HBSS they are suspeneded in minimum essential medium (MEM) and passed through a glass wool column to remove macrophages. The cells are then incubated on a nylon wool column at 37° C., 95% air, 5% $CO_2$, for 45 minutes. The nonadherant T lymphocytes are then eluted from the column, counted, and adjusted to $20 \times 10^6$ cells/ml. 50 µl. of cells are cultured (37° C., 95% air, 5% $CO_2$) with a suboptimal concentration of Concanavalin A plus compound, for 48 hours before addition of 0.5 µCi. of 3H-thymidine for the last 16 hours of culture. The total volume of the culture system is 200 µl. The cells are then harvested on a multiple automatic sample harvestor (Mash II), the glass fiber filter disks placed in 10 ml. of xylene base scintillation fluid, and counted for 1 minute in a liquid scintillation counter. Results are reported as CPM ±SE. Comparisons are made between counts obtained with control cultures and cultures containing compound and a determination made as to whether the compounds are active at the dosage tested.

The results are summarized below:

| Compound | Concentration (μg/culture) | 3H-Thymidine Uptake CPM ± S.E. | p |
| --- | --- | --- | --- |
| Concanavalin A | 0.025 | 9859 ± 710 | — |
| Concanavalina A + 3-(4-chlorophenyl)-2,3-dihydro-3-hydroxy-5-oxo-5H-thiazolo[2,3-b]quinazoline-2-acetic acid | 0.5 | 5427 ± 1051 | <0.01 |
|  | 1.0 | 6650 ± 373 | <0.001 |

The results show that at low dosage levels the compound tested significantly inhibits the proliferation of T cells stimulated by the mitogen, Concanavalin A, evidencing a strong suppressor activity.

What is claimed is:

1. A compound of the formula:

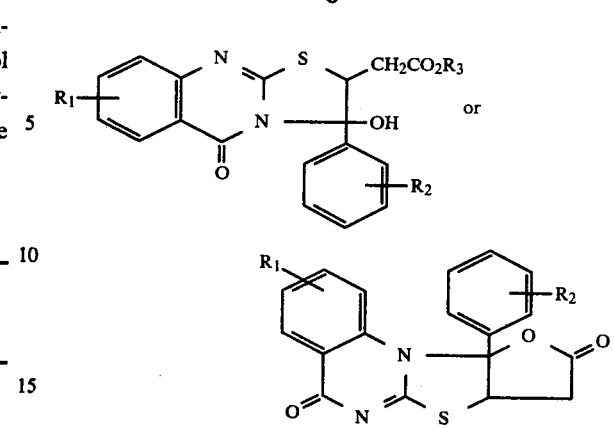

wherein
$R_1$ is hydrogen, lower alkyl of 1–4 carbon atoms, $CF_5$, $NO_2$ or $NH_2$;
$R_2$ is hydrogen, lower alkyl of 1–4 carbon atoms, $CF_3$, halo, cyclohexyl or phenyl; and
$R_3$ is hydrogen or lower alkyl of 1–4 carbon atoms.

2. The compound of claim 1, which is 3-(4chlorophenyl)-2,3-dihydro-3-hydroxy-5-oxo-5H-thiazole[2,3-b]quinazoline-2-acetic acid.

3. The compound of claim 1, which is 10a-(4-chlorophenyl)-7a,10a-dihydro-5H-furo[2′,3′;4,5]thiazolo[3,2-a]-quinazoline-5,9-(8H)-dione.

* * * * *